United States Patent [19]

Bartholomew

[11] Patent Number: 5,400,776
[45] Date of Patent: Mar. 28, 1995

[54] APPARATUS FOR MAINTAINING A BEND IN A MEDICAL INSUFFLATION TUBE

[75] Inventor: Donald D. Bartholomew, Mt. Clemens, Mich.

[73] Assignee: Proprietary Technology, Inc., Southfield, Mich.

[21] Appl. No.: 88,385

[22] Filed: Jul. 9, 1993

[51] Int. Cl.⁶ ............... A61M 25/04; A61M 31/00
[52] U.S. Cl. ............... 128/200.24; 128/207.18; 604/174; 604/177
[58] Field of Search ............... 128/200.24, 207.18, 128/207.17, 207.14, 207.15, DIG. 26; 351/122; 604/174, 177

[56] References Cited

U.S. PATENT DOCUMENTS

| | | | |
|---|---|---|---|
| 619,163 | 2/1899 | Gieberich | 351/122 |
| 2,168,705 | 8/1939 | Francisco et al. | 128/207.18 |
| 2,502,734 | 4/1950 | Lyons | 351/122 |
| 4,435,174 | 3/1984 | Redmond et al. | 604/174 |
| 4,465,067 | 8/1984 | Koch et al. | 128/207.18 |
| 4,535,767 | 8/1985 | Tiep et al. | 128/207.18 |
| 4,559,941 | 12/1985 | Timmons et al. | 128/207.18 |
| 4,572,177 | 2/1986 | Tiep et al. | 128/205.17 |
| 4,662,729 | 5/1987 | Dobson | 351/123 |
| 4,699,139 | 10/1987 | Marshall et al. | 128/207.18 |
| 5,025,805 | 6/1991 | Nutter | 128/207.18 |
| 5,193,534 | 3/1993 | Peppler | 128/207.18 |

Primary Examiner—Edgar S. Burr
Assistant Examiner—William J. Deane, Jr.
Attorney, Agent, or Firm—Harness, Dickey & Pierce

[57] ABSTRACT

The present invention apparatus (11) maintains a curved shape in a portion of a medical insufflation tube (15) and comprises a formable longitudinal semi-cylindrical member (39) having a longitudinal edge (57) thereon and a pair of collar elements (41 and 43) radially continuing therearound further than the longitudinal semi-cylindrical member (39). The formable clip apparatus (11) substantially encases and maintains a longitudinal bend (59) in the portion of the insufflation tube (15) that fits behind each of the patient's ears.

In accordance with another aspect of the present invention, a fastener (13) retains a medical insufflation tube (15) to a patient's clothing (101) and is comprised of an annular-shaped portion (83) having an aperture (85) therein and an orifice (89) allowing entry thereto for circumferential engagement with the tube (15). The fastener (13) is further comprised of an integral pincer portion (91) having a pair of flexible inwardly angled legs (93 and 95), for attachment to the patient's clothing (101).

8 Claims, 1 Drawing Sheet

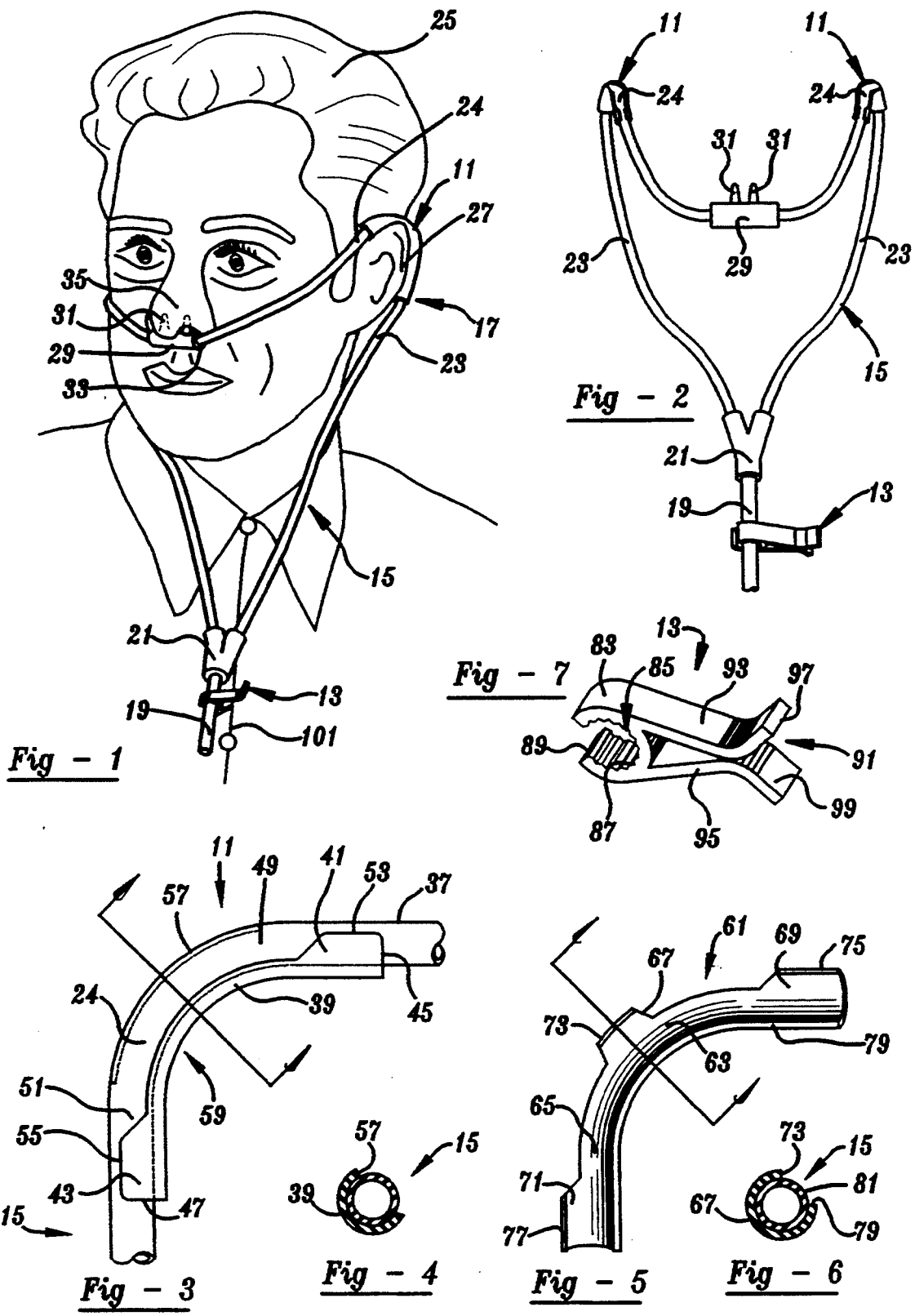

APPARATUS FOR MAINTAINING A BEND IN A MEDICAL INSUFFLATION TUBE

BACKGROUND OF THE INVENTION

This invention relates generally to an apparatus for maintaining a longitudinal bend in a medical insufflation tube and specifically to a formable clip apparatus which maintains a predetermined bend in a portion of the insufflation tube which fits behind a patient's ear. This invention also specifically relates to a fastener for retaining a portion of an insufflation tube to a patient's clothing.

Various respiratory ailments require the administration of oxygen to a patient over an extended period of time. Conventionally, one such device which supplies oxygen to a patient consists of a flexible pair of polyvinyl chloride (PVC) tubes which are centrally joined by a rigid sleeve member having a pair of cannula extending upward therefrom. These cannula are inserted into the nostrils of the patient. Each of the connected flexible tubes run along the patient's cheek, drape over the patient's ear and are joined to a single tube which is connected to an oxygen supply. However, such an oxygen insufflation device can easily be pulled to one side of the patient's face or another thereby disorienting the pair of cannula within the patient's nostrils. This causes great discomfort to the wearer of such an insufflation system and often causes facial sores.

A number of improvements have attempted to relieve this orientation problem as well as the discomforting irritations and sores. A first method uses soft pads and is shown in: U.S. Pat. No. 5,025,805 entitled "Nasal Cannula Assembly," issued to Nutter on Jun. 25, 1991; and, U.S. Pat. No. 4,699,139 entitled "Nasal Cannula Assembly with Patient Comfort Pad," issued to Marshall et al. on Oct. 13, 1987, both of which are incorporated by reference herewithin. Another method uses eyeglass frame-type devices and is shown in: U.S. Pat. No. 4,559,941 entitled "Eyeglass Frame and Nasal Cannula Assembly," issued to Timmons et al. on Dec. 24, 1985; U.S. Pat. No. 4,465,067 entitled "Oxygen Insufflation Device," issued to Koch et al. on Aug. 14, 1984; and U.S. Pat. No. 2,168,705 entitled "Nasal Inhaler," issued to Francisco et al. on Aug. 8, 1939. A third method is depicted in U.S. Pat. No. 4,572,177 entitled "Oxygen Therapy Apparatus," issued to Tiep et al. on Feb. 25, 1986, incorporated by reference herewith. Although these patents illustrate improvements in the art, they do not cost effectively solve the orientation discomfort problem.

SUMMARY OF THE INVENTION

In accordance with the present invention, the preferred embodiment of an apparatus for maintaining a curved shape in a portion of a medical insufflation tube comprises a formable longitudinal semi-cylindrical member having a longitudinal edge thereon and a pair of collar elements radially continuing therearound further than the longitudinal semi-cylindrical member. This formable clip apparatus substantially encases and maintains a longitudinal bend in the portion of the insufflation tube that fits behind each of the patient's ears. As a consequence, the present invention acts to properly oriented the insufflation tube about the patient's nostrils such that the traditional discomfort caused by disorientation of the tube and the attached cannula is significantly reduced.

In accordance with another aspect of the present invention, the preferred embodiment of a fastener for use in retaining a medical insufflation tube to a patient's clothing is comprised of an annular-shaped portion having an aperture therein and an orifice allowing entry thereto for circumferential engagement of the tube. The fastener is further comprised of an integral pincer portion having a pair of flexible inwardly angled legs, for attachment to the patient's clothing. This fastener serves to orient the medical insufflation tube centrally about the patient's body.

Additional advantages and features of the present invention will become apparent from the following description and appended claims, taken in conjunction with the accompanying drawings.

BRIEF DESCRIPTION OF THE DRAWINGS

FIG. 1 is a perspective view showing a patient wearing a medical insufflation tube having a formable clip apparatus and fastener of the present invention;

FIG. 2 is a front elevation view of the present invention formable clip apparatus and fastener in relation to the medical insufflation tube of FIG. 1;

FIG. 3 is a side elevation view of the present invention formable clip apparatus in relation to the medical insufflation tube of FIG. 1;

FIG. 4 is a cross sectional view of the present invention formable clip apparatus in relation to the medical insufflation tube, taken along line 4—4 from FIG. 3;

FIG. 5 is a side elevation view showing a second preferred embodiment of the present invention formable clip apparatus of FIG. 1;

FIG. 6 is a cross sectional view showing the second preferred embodiment of the present invention formable clip apparatus in relation to the medical insufflation tube, taken along line 6—6 from FIG. 5; and FIG. 7 is a perspective view of the present invention fastener of FIG. 1.

DETAILED DESCRIPTION OF THE PREFERRED EMBODIMENTS

Referring to FIGS. 1 and 2, a preferred embodiment of the present invention apparatus 11 and fastener 13 are used in combination with a medical insufflation tube 15. This insufflation tube 15 is used to provide oxygen to a patient 17.

Insufflation tube 15 is comprised of a main tube portion 19 which is connected to an oxygen supply (not shown) and has a splitting connector 21 attached thereupon. Connector 21 is Y-shaped and is joined to a pair of branched tube portions 23 which run along either side of patient's head 25. A bent tube portion 24 of each branched portion 23 fits between patient's head 25 and an auricle portion 27 of patient's ear. Each branched portion 23 then extends downward and across the patient's face where they mate with a centrally located sleeve member 29 which has a pair of cannulas 31 upwardly extending therefrom. Each cannula 31 fits into a nostril 33 of the patient's nose 35. Thus, oxygen is supplied to the patent 17.

A first preferred embodiment of formable clip apparatus 11 fits around a substantial portion of the outer surface 37 of bent tube portion 24. This can best be seen in FIGS. 3 and 4. Formable clip 11 has a longitudinal semi-cylindrical center member 39 which peripherally encases approximately half of the cross sectional circumference of insufflation tube 15. Formable clip 11 further has a pair of collar elements 41 and 43 each of which border longitudinal semi-cylindrical member 39 and forme ends 45 and 47. These collar elements 41 and 43 are substantially cylindrical in cross sectional shape and radially encase approximately three-quarters of the circumference of insufflation tube 15. Collar elements 41 and 43 may fit around the inside (as shown in FIG. 3) or outside (not shown) of the bend in tube 15. Nevertheless, gaps 49 and 51 are formed between edges 53 and 55, respectively, of collar elements 41 and 43, respectively, and a longitudinal edge 57 of longitudinal semi-cylindrical member 39. As illustrated most clearly in FIG. 6, the edges 53 and 55 extend well beyond a 180° radius, while the longitudinal edge 57, as shown most clearly in FIG. 4, extends to a radius of approximately 180° and to a radius which is less than the edges 53 and 55 of the collar elements. Accordingly, insufflation tube 15 can be compressibly inserted through gaps 49 and 51, and within formable clip 11. Formable clip 11 also has a longitudinal bend 59 of approximately 90° but may vary depending on the comfort and orientation desired by patient 17. Formable clip 11 may be attached to the outside or the inside of the bend in tube 15.

Referring to FIGS. 5 and 6, a second preferred embodiment of a present invention formable clip apparatus 61 is shown. Formable clip 61 has a pair of longitudinal semi-cylindrical members 63 and 65 which are separated by a collar element 67 therebetween. Furthermore, collar elements 69 and 71 border longitudinal semi-cylindrical members 63 and 65, respectively, at the ends thereof. Collar elements 67, 69 and 71 are all substantially cylindrical in cross sectional shape and radially extend around a majority of the cross sectional circumference of insufflation tube 15. Moreover, collar element 67 has an edge 73, collar element 69 has an edge 75, and collar element 71 has an edge 77 thereupon. Oppositely, formable clip 61 has a longitudinal edge 79 created along the inside radius of the part. A gap 81 is created between collar edges 73, 75 and 77, and longitudinal edge 79; thus, insufflation tube 15 can be compressibly inserted therewithin. Formable clips 11 and 61 are made from a stamped metallic material.

The preferred embodiment of fastener 13 of the present invention can best be observed in FIGS. 1, 2 and 7. Fastener 13 has an annular-shaped portion 83 with a circular aperture 85 centrally located therein. Aperture 85 forms an inside surface 87 therearound which may be grooved to provide greater frictional retention. Furthermore, an orifice 89 severs a portion of annular-shaped portion 83 such that main tube portion 19 of insufflation tube 15 can be compressibly inserted therein. A pincer portion 91 is integrally attached to annular-shaped portion 83. Pincer portion 91 is comprised of a pair of inwardly angled legs 93 and 95. These legs 93 and 95, are made of a flexible polymeric material such that the material's modulus of elasticity and any structural ribs (not shown) will forcibly compress legs 93 and 95 against one another. Legs 93 and 95 also have a lead-in portion 97 and 99, respectively, outwardly extending therefrom. Therefore, legs 93 and 95 of fastener 13 serve to trap a portion of the patient's clothing 101 therebetween. Accordingly, fastener 13 centrally orients insufflation tube 15 about the body of patient 17.

It will be appreciated that the formable clip apparatus and the fastener of the present invention represent significant improvements for orienting medical insufflation tubes and for providing greater patient comfort. While a number of specific embodiments of the present invention have been disclosed, it will be appreciated that various modifications may be made without departing from the present invention. For example, more than three collar elements may be incorporated within the formable clip. Furthermore, one skilled in the art will appreciate that a foam cushioning pad may be attached around the outside of the formable clips without departing from the present invention. While various materials have been disclosed in an exemplary fashion, various other materials may of course be employed. It is intended by the following claims to cover these and any other departures from these disclosed embodiments which fall within the true spirit of this invention.

I claim:

1. A metallic apparatus which can be shaped to a desired form and is useful for maintaining a curved shape in a preselected portion of a medical insufflation tube, said preselected portion being disposable between the auricle portion of a person's ear and the person's head, said apparatus being comprised of:
   at least two spaced apart collar elements being partially cylindrical in cross sectional shape and having first edges thereupon which extend beyond a 180° radius,
   at least one elongated member which joins said collar elements thereon, said elongated member having a second longitudinal edge thereupon which extends to a radius of approximately 180° such that said first edges of said collar elements and said second edge of said elongated member cooperatively assist in maintaining the insufflation tube, said apparatus having an elongated bend extending between said collar elements and being suitable for substantially encasing said preselected portion of said insufflation tube.

2. The apparatus of claim 1 wherein said at least two spaced apart said collar elements include a first collar element disposed proximate to one end of the apparatus and a second collar element disposed proximate to the other end of said apparatus with a third collar element being centrally located between said first and second collar elements and being located centrally along said elongated bend of said apparatus, wherein said plurality of collar elements are joined by said elongated member.

3. A formable apparatus for maintaining a portion of an insufflation tube in an arcuate shape, said apparatus being comprised of a formable clip including a plurality of spaced apart collar elements being partially cylindrical in cross sectional shape and having first edges thereupon which extend beyond a 180° radius, and a elongated member having a second longitudinal edge thereupon which extends to a radius of approximately 180° such that said first edges of the collar elements and the second edge of said elongated member include a gap for receiving the insufflation tube.

4. The apparatus of claim 3 wherein said plurality of collar elements include a first collar element disposed along one end of the apparatus and a second collar element disposed along a second end of the apparatus.

5. The apparatus of claim 4 wherein a third collar element is disposed between said first and second collar elements along said elongated member.

6. The apparatus of claim 5 wherein said third collar element is centrally located along said elongated member.

7. The apparatus of claim 1, in combination with a separate fastener for maintaining the insufflation tube in proximity to the wearer, said fastener including an annular shaped portion for receiving the insufflation tube and a pincer portion extending from said annular shaped portion which includes a pair of inwardly angled legs forcibly compressed against each other, whereby said legs can be selectively separated for attachment to the wearer's clothing.

8. The apparatus of claim 3, in combination with a separate fastener for maintaining the insufflation tube in proximity to the wearer, said fastener including an annular shaped portion for receiving the insufflation tube and a pincer portion extending from said annular shaped portion which includes a pair of inwardly angled legs forcibly compressed against each other, whereby said legs can be selectively separated for attachment to the wearer's clothing.

* * * * *